US00PP27327P2

(12) United States Plant Patent
Bacon

(10) Patent No.: US PP27,327 P2
(45) Date of Patent: Nov. 1, 2016

(54) PLUM TREE NAMED 'SUPLUMFIFTY'

(50) Latin Name: *Prunus salicina*
Varietal Denomination: Suplumfifty

(71) Applicant: Sun World International, LLC, Bakersfield, CA (US)

(72) Inventor: Terry A. Bacon, Bakersfield, CA (US)

(73) Assignee: Sun World International, LLC, Bakersfield, CA (US)

( * ) Notice: Subject to any disclaimer, the term of this patent is extended or adjusted under 35 U.S.C. 154(b) by 21 days.

(21) Appl. No.: 14/545,357

(22) Filed: Apr. 27, 2015

(51) Int. Cl.
*A01H 5/08* (2006.01)

(52) U.S. Cl.
USPC ..... Plt./184

(58) Field of Classification Search
USPC ..... Plt./184
See application file for complete search history.

*Primary Examiner* — Annette Para
(74) *Attorney, Agent, or Firm* — Knobbe, Martens, Olson & Bear, LLP

(57) ABSTRACT

A new and distinct plum tree variety, *Prunus salicina*, cv. 'Suplumfifty' is characterized by fruit having deep red flesh, nearly black skin, and a cling stone. The fruit is medium in sugar and has low acidity. The fruit of the new variety 'Suplumfifty' is also moderate in juice and has a sweet-mild flavor. The date of the harvest of the fruit of the new variety is later than for 'Black Splendor' (unpatented). The fruit of the new variety 'Suplumfifty' ripens with nearly same timing as the fruit of 'Black Kat' (U.S. Plant Pat. No. 13,134) but with a deep red flesh compared to amber-colored for 'Black Kat'.

1 Drawing Sheet

Latin name of the genus and species claimed: *Prunus salicina.*

Variety denomination: 'Suplumfifty'.

BACKGROUND AND SUMMARY OF THE INVENTION

This invention relates to the discovery and asexual propagation of a new and distinct variety of plum, *Prunus salicina* cv. 'Suplumfifty'. The new variety was first originated by hybridization by Terry A. Bacon as breeder number 'PL1387RB'.

The new variety 'Suplumfifty' is characterized by having fruit with deep red flesh, nearly black skin, and a cling stone. The fruit is medium in sugar and has low acidity. The fruit of the new variety 'Suplumfifty' is also moderate in juice and has a sweet-mild flavor.

The seed parent is '98P039-035-291' (unpatented breeding variety), and the pollen parent is '96P024-003-430' (unpatented breeding variety). The parent varieties were first crossed in February 2008, with the date of first sowing being March 2009, and the date of first flowering being February 2011. The new plum variety 'Suplumfifty' was first asexually propagated by Terry Bacon near Wasco, Kern County, Calif. in January 2012 by grafting.

The new variety 'Suplumfifty' is distinguished from its seed parent '98P039-035-291' (unpatented breeding variety) in that the new variety 'Suplumfifty' has fruit with deep red flesh while the fruit of '98P039-035-291' has yellow flesh.

The new variety 'Suplumfifty' is similar to its pollen parent '96P024-003-430' (unpatented breeding variety) in that the fruit of both varieties has red flesh. The new variety 'Suplumfifty' is distinguished from its pollen parent '96P024-003-430' in that the harvest of the fruit of the new variety 'Suplumfifty' starts later, on August 11, compared to July 20 for '96P024-003-430'.

The fruit of the new variety 'Suplumfifty' ripens with nearly same timing as the fruit of 'Black Kat' (U.S. Plant Pat. No. 13,134) but the flesh color of the fruit of the new variety 'Suplumfifty' is red compared to amber-colored for 'Black Kat' (U.S. Plant Pat. No. 13,134). The fruit of teh new variety 'Suplumfifty' has deep red flesh like 'Black Splendor' (unpatented) but the harvest of the fruit of the new variety 'Suplumfifity' starts August 11 while the 'Black Splendor' harvest starts June 12.

The new variety 'Suplumfifty' has been shown to maintain its distinguishing characteristics through successive asexual propagations by, for example, grafting and budding.

BRIEF DESCRIPTION OF THE PHOTOGRAPH

The accompanying color photographic illustration FIG. 1 shows typical specimens of the foliage and fruit of the present new plum variety 'Suplumfifty'. The illustration shows the upper and lower surface of the leaves, a view of the fruit as a whole, the stone as a whole, and a sectional view of a fruit divided across its suture plane to show flesh color, pit cavity and the stone remaining in place.

The photographic illustration was taken shortly after being picked and the colors are as nearly true as is reasonably possible in a color representation of this type. The photographs depicts fruit and vegetative growth from a four year old tree.

DETAILED DESCRIPTION OF THE PREFERRED EMBODIMENT

Throughout this specification, color names beginning with a small letter signify that the name of that color, as used in common speech is aptly descriptive. Color names beginning with a capital letter designate values based upon The R.H.S. Colour Chart published by The Royal Horticultural Society, London, England, 1986.

The descriptive matter which follows pertains to four year old 'Suplumfifty' plants, grown in the vicinity of Wasco, Kern County, Calif., during 2014 and is believed to apply to plants of the variety grown under similar conditions of soil and climate elsewhere.

TREE

General: (Measurements taken on a four year old tree unless otherwise noted.).

*Size*.—Medium, reaches a height of approximately 3 meters including normal pruning.

*Spread*.—Approximately 3 meters.

*Vigor*.—Medium, growth of about 1.5 m to 2 m in height the first growing season.

*Growth*.—Upright.

*Productivity*.—Productive.

*Form*.—Vase formed.

*Bearer*.—Regular.

*Fertility*.—Unknown.

*Canopy density*.—Medium.

*Hardiness*.—Hardy in all fruit growing areas of California. Winter chilling requirement is approximately 700 hours at or below 7.2° C.

*Disease resistance/susceptibility*.—Under close observation in Kern County, Calif., no particular plant/fruit disease resistance/susceptibility has been observed.

*Insect resistance/susceptibility*.—Under close observation in Kern County, Calif., no particular plant/fruit insect resistance/susceptibility has been observed.

Trunk: (Measurements at approximately 30 cm above soil line on mature tree).

*Length*.—46 cm.

*Diameter*.—Approximately 14 cm.

*Texture*.—Medium shaggy, increases with age of tree.

*Trunk color*.—About Medium Greyed-Green 198B on older weathered wood and about Medium Greyed-Orange 173B on younger, less weathered wood.

Branches: (Measurements at approximately 90 cm above soil line.).

*Length*.—2 m.

*Size*.—Diameter approximately 8 cm.

*Texture*.—Medium, Shaggy.

*Color*.—Varying between about Medium Greyed-Green 198B to about Medium Greyed-Orange 173B, becoming darker with age.

*Lenticels*.—Present.

Lenticels:

*Number*.—Medium. 1/cm2.

*Density*.—About 2/cm$^2$.

*Color*.—About Medium Grey-Brown 199B.

*Size*.—Medium. Approximately 3 mm×2 mm.

Flowering shoots: (Data taken in September at mid-point of current season growth.).

*Size*.—Average diameter approximately 5 mm.

*Color*.—Topside: About Dark Greyed-orange 176A. Underside: About Dark Greyed-Orange 176A.

*Internode length*.—Medium; approximately 2 cm. Midway on flowering shoot.

*Flowering shoot lenticels*.—Moderate amount. 3/cm2. Color: About Medium Greyed-Orange 164B. Diameter: Approximately 0.5 mm.

*Flowering shoot leaf buds*.—Shape: Conical. Width: Approximately 1.5 mm. Length: Approximately 2 mm. Color: About Dark Greyed-Orange 166A. Texture: Smooth.

*Flowering shoot flower buds*.—Shape: Ovoid. Width: Approximately 1.1 mm. Length: Approximately 2 mm. Color: About Dark Greyed-Orange 166A. Number of buds per node: 2-4. Texture: Smooth.

*Density of buds*.—Medium.

*Flower bud distribution*.—On spurs and one year old shoots and older wood.

*Ratio of wood (leaf) buds to flowering buds*.—½-4 on nodes.

*Anthocyanin intensity*.—Slight on upper surface of shoot.

*Spur length*.—Usually 9 mm.

*Position of vegetative bud in relation to shoot*.—Slightly held out.

FOLIAGE

Leaves: (Data taken in September on fully expanded leaves at mid-point of the current season growth.).

*Average length*.—Medium; approximately 90 mm without petiole.

*Average width*.—Medium; approximately 45 mm.

*Thickness*.—Medium. 1 mm.

*Color*.—Upper surface: About Dark Green 139A. Lower surface: About Medium Green 139B.

*Form*.—Broad obovate.

*Tip*.—Cuspidate.

*Base*.—V-shaped.

*Margin*.—Crenate.

*Venation*.—Pinately net veined.

*Vein color*.—About Medium Green 146D.

*Surface texture*.—Smooth, upper and lower surfaces.

*Leaf blade (ratio of length to width)*.—Medium, about 2:1.

*Shape in the cross section*.—Concave.

*Angle at apex*.—Small.

*Profile*.—Up folded.

*Leaf blade tip*.—Curved downwardly.

*Angle of tip*.—Acute.

*Undulation of margin*.—Slight.

*Glossiness of upper side*.—Slight.

*Density of pubescence of lower side*.—Absent.

Petiole:

*Average length*.—Short; approximately 8 mm.

*Average diameter*.—Medium, approximately 2 mm.

*Color*.—About Medium Green 146D with highlights of about Medium Red 43B.

*Thickness*.—Medium, approximately 2 mm.

*Texture*.—Smooth.

*Length*.—10 mm.

Stipules:

*Number/leaf bud*.—Approximately 0-2 per leaf bud when present.

*Typical length*.—Approximately 8 mm.

*Color*.—About Medium Yellow-Green 147C.

*Persistence*.—Falls off.

*Texture (upper)*.—Smooth on upper and lower surfaces.

Leaf glands:

*Average number*.—Approximately 0.

FLOWERS

General:

*Flower blooming period*.—First bloom: Approximately March 1 in Wasco, Calif. Full bloom: Approximately March 5 in Wasco, Calif.

*Location of first bloom*.—Bottom of third canopy.

*Location of full bloom*.—Mid-section of the canopy.

*Duration of bloom*.—Medium; approximately 9 days.

*Diameter of fully opened flower*.—Medium, approximately 26 mm.

*Flower aroma*.—Slight.
*Shape*.—Campanulate.
Peduncle:
*Length*.—Medium; approximately 10 mm.
*Diameter*.—Slender; approximately 1.5 mm.
*Color*.—About Light Green 139D.
*Pubescence*.—Absent.
Petals:
*Number*.—5.
*Arrangement*.—Free.
*Length*.—Approximately 11 mm.
*Diameter*.—Approximately 8 mm.
*Shape*.—Obovate.
*Apex shape*.—Rounded.
*Base shape*.—Narrows at point of attachment.
*Color of inner and outer surface*.—About White 155B.
*Surface texture*.—Smooth.
*Margins*.—Slightly undulating, entire.
*Frequency of flowers with double petals*.—None.
*Claw length*.—Short, 2 mm.
*Margin waviness*.—Medium.
*Base angle*.—Medium.
*Division of upper margin*.—Entire.
*Pubescence of inner surface*.—Absent.
*Pubescence of outer surface*.—Absent.
Sepals:
*Number*.—5.
*Length*.—Approximately 4 mm.
*Diameter*.—Approximately 3 mm.
*Shape*.—Elliptic.
*Color*.—About Medium Yellow-Green 145A.
*Surface texture*.—Smooth.
*Margins*.—Finely toothed.
*Positioning*.—Adpressed to petals.
*Pubescence of inner surface*.—Absent.
*Pubescence of outer surface*.—Absent.
*Frequency of flowers with double sepals*.—None.
Stamens:
*Number*.—Usually 28-35, average 32.
*Average length*.—About 5-10 mm, average about 7 mm.
*Filament color*.—About White 155B.
*Anther color*.—About Medium Yellow 8A, becoming dark as it ages to Medium Greyed-Orange 163A.
*Flower pollen color*.—About Medium Greyed-Orange 163A.
*Position*.—Perigynous.
Pistil:
*Color*.—About Light Yellow-Green 144D.
*Number*.—Usually one, ocassionally 2.
*Average length*.—Approximately 6-9 mm.
*Ovary diameter*.—Approximately 1 mm.
*Pubescence*.—None.
*Stigma extension in comparison to anthers*.—Usually below.
*Style frequency of supplementary pistils*.—Few.
Flower-buds:
*Hardiness*.—Somewhat hardy.
Receptacle:
*Depth*.—Medium, 5 mm.
*Pubescence of inner surface*.—Absent.
*Pubescence of outer surface*.—Absent.
Ovary:
*Color*.—About Light Yellow-Green 144D.
Style:
*Pubescence (of base)*.—Absent.

FRUIT

General: (Description taken near Wasco, Kern County, Calif. on August 16).
*Date of first pick*.—Approximately August 12.
*Date of last pick*.—Approximately August 31.
*Maturity when described*.—Firm.
*Season ripening*.—Late. August 12.
*Position of maximum diameter*.—Towards the middle.
*Symmetry about the suture*.—Symmetric.
*Shape of base*.—Rounded.
Size:
*Length (stem end to apex)*.—Approximately 66 mm.
*Diameter in line with suture plane*.—Approximately 70 mm.
*Diameter perpendicular to suture plane*.—Approximately 70 mm.
*Average weight*.—Approximately 176 gm.
Form:
*Viewed from apex*.—Rounded.
*Viewed from side, facing suture*.—Rounded.
*Viewed from side, perpendicular to suture*.—Rounded.
Apex shape: Rounded.
Fruit stem cavity:
*Shape*.—Rounded.
*Depth*.—Shallow; Approximately 0.8 cm.
*Breadth*.—Approximately 8 cm.
*Width*.—Medium, 14 mm.
Fruit stem:
*Length*.—Medium; approximately 2 mm.
*Diameter*.—Approximately 3 mm.
*Color*.—About Light-Yellow-Green 147D.
*Adherence to stone*.—Strong.
Fruit skin:
*Thickness*.—Medium, 0.8 mm.
*Adherence to flesh*.—Strong.
*Surface texture*.—Smooth.
*Pubescence*.—None.
*Bloom*.—Medium, somewhat persistent.
*Ground color*.—About Medium Greyed-Red 180B when visible.
*Overcolor*.—About Dark Black 202A.
*Relative area of overcolor*.—Nearly 100%.
*Pattern of overcolor*.—Solid.
*Taste*.—Neutral.
*Reticulation*.—Absent.
*Roughness*.—Absent.
*Tenacity*.—Tenacious to flesh.
*Tendency to crack*.—Slight to none in wet season.
Flesh:
*Ripens*.—Evenly.
*Texture*.—Firm-juicy.
*Fibers*.—Few.
*Flavor*.—Sweet-mild.
*Brix*.—Approximately 20°.
*Juice*.—Moderate.
*Aroma*.—Slight.
*Anthocyanin color around stone*.—About Dark Red 46A.
*Anthocyanin color of flesh*.—Strongly expressed throughout evenly.
*Amygdalin*.—Wanting.

*Acidity*.—Low.
*Sugar content*.—High.
*Eating quality*.—Good.
*Stone/flesh ratio*.—Small, about 1:98.
*Firmness*.—Firm.

Pit cavity size:
*Length*.—Approximately 28 mm.
*Diameter perpendicular to suture plane*.—Approximately 18 mm.
*Diameter in line with suture*.—Approximately 8 mm.
*Color*.—About Dark Red 46A.

Fruit use: Fresh market.

Fruit shipping and keeping quality: Good.

Stone:
*Stone freeness*.—Cling over the entire surface.
*Degree of adherence to flesh*.—Strong.
*Stone size*.—Size: Medium. Size compared to Fruit: Small. Length: Medium, approximately 28 mm. Diameter in line with suture plan: Approximately 18 mm. Diameter perpendicular to suture plane: Approximately 8 mm. Width of Stalk End: Medium, Approximately 3 cm. Angle of Stalk end: Right angle. Hilum: Oval.
*Stone form*.—Viewed from side: Oval with flat base and pointed apex. Viewed from ventral end: Flattened. Viewed from Stem end: Oval.
*Stone shape*.—Base shape: Nearly straight. Apex shape: Pointed.
*Hilum*.—Oval.
*Stone surface*.—Irregularly furrowed and pitted throughout.
*Stone halves*.—Nearly symmetrical.
*Stone ridges*.—Rounded throughout.
*Stone outgrowing keel*.—Partly developed.
*Stone tendency to split*.—None in wet season.
*Stone color*.—About Medium Greyed-Orange 164C.
*Position of maximum*.—Middle.
*Sides*.—Somewhat equal.
*Pits*.—Irregular.
*Ventrical edge*.—Thin with slight wing toward middle.
*Dorsal edge*.—Irregular ridges on either side.

What is claimed is:

1. A new and distinct plum tree as herein described and illustrated.

* * * * *

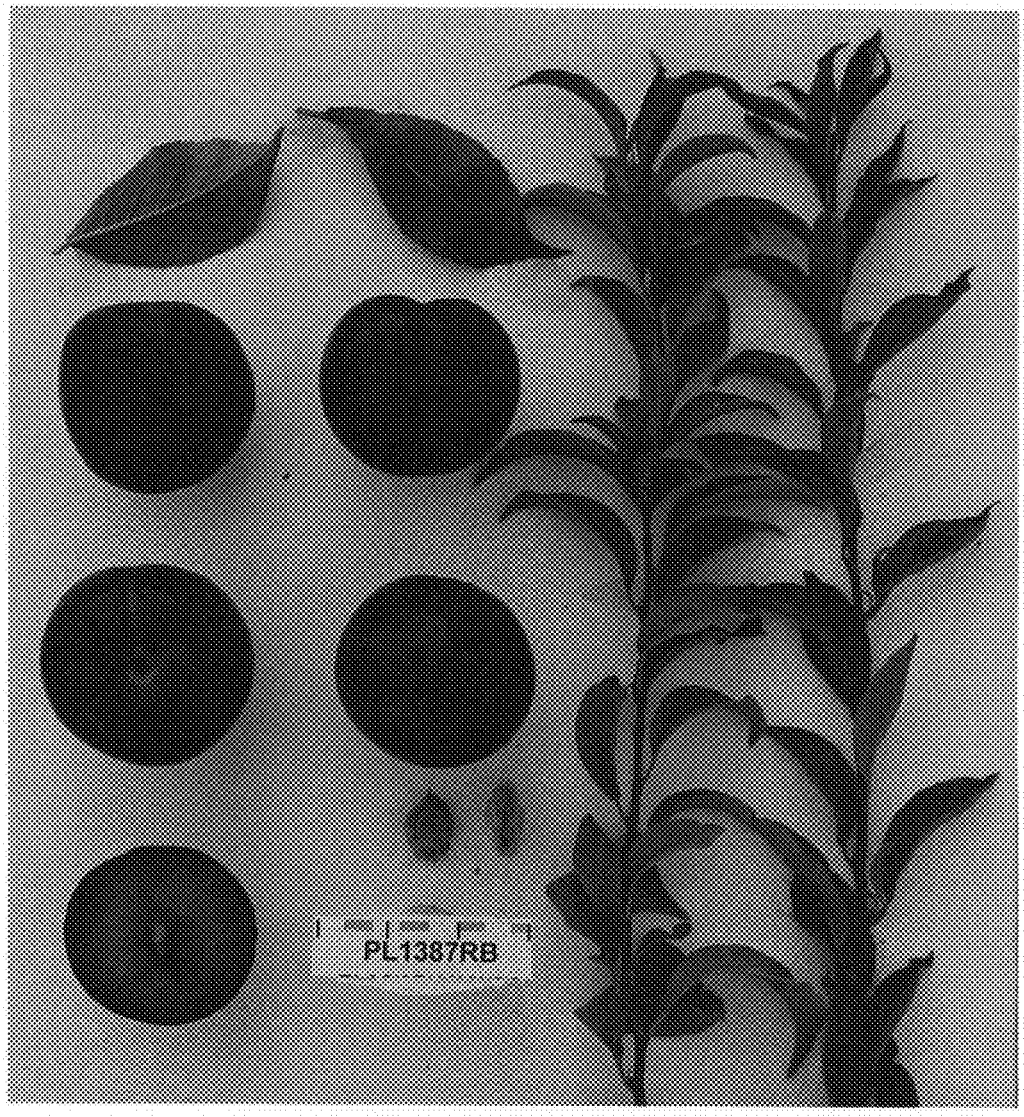
PL1387RB